US006783992B2

(12) United States Patent
Robotti et al.

(10) Patent No.: US 6,783,992 B2
(45) Date of Patent: Aug. 31, 2004

(54) METHODS AND USING CHEMICO-MECHANICAL MICROVALVE DEVICES FOR THE SELECTIVE SEPARATION OF COMPONENTS FROM MULTI-COMPONENT FLUID SAMPLES

(75) Inventors: Karla M. Robotti, Mountain View, CA (US); Hongfeng Yin, Cupertino, CA (US)

(73) Assignee: Agilent Technologies, Inc., Palo Alto, CA (US)

( * ) Notice: Subject to any disclaimer, the term of this patent is extended or adjusted under 35 U.S.C. 154(b) by 425 days.

(21) Appl. No.: 09/754,687

(22) Filed: Jan. 3, 2001

(65) Prior Publication Data

US 2002/0121487 A1 Sep. 5, 2002

(51) Int. Cl.⁷ .......................... G01N 1/18; G01N 27/26; G01N 27/27; B01L 11/00
(52) U.S. Cl. ...................... 436/177; 436/178; 204/455; 204/605; 422/101
(58) Field of Search ........................... 422/99, 101, 57, 422/103; 204/455, 605, 604, 453; 210/656; 436/177, 178, 180; 137/828, 807

(56) References Cited

U.S. PATENT DOCUMENTS

| | | | |
|---|---|---|---|
| 4,439,966 A | | 4/1984 | Alles |
| 5,051,237 A | * | 9/1991 | Grenner et al. ............... 422/56 |
| 5,162,582 A | | 11/1992 | Ito et al. |
| 5,298,260 A | | 3/1994 | Viegas et al. |
| 5,422,271 A | * | 6/1995 | Chen et al. ............... 435/287.2 |
| 5,432,245 A | | 7/1995 | Roberts et al. |
| 5,470,445 A | | 11/1995 | Murray et al. |
| 5,480,614 A | | 1/1996 | Kamahori |
| 5,543,838 A | | 8/1996 | Hosier et al. |
| 5,569,364 A | | 10/1996 | Hooper et al. |
| 5,571,410 A | | 11/1996 | Swedberg et al. |
| 5,587,128 A | * | 12/1996 | Wilding et al. ............... 422/50 |
| 5,593,559 A | * | 1/1997 | Wiktorowicz ............... 204/453 |
| 5,605,662 A | | 2/1997 | Heller et al. |
| 5,631,337 A | | 5/1997 | Sassi et al. |
| 5,645,702 A | | 7/1997 | Witt et al. |
| 5,653,859 A | | 8/1997 | Parton et al. |
| 5,653,939 A | | 8/1997 | Hollis et al. |
| 5,658,413 A | | 8/1997 | Kaltenbach et al. |
| 5,658,981 A | | 8/1997 | Ohsumi |
| 5,670,480 A | | 9/1997 | Hogan, Jr. |
| 5,672,656 A | | 9/1997 | Murayama et al. |

(List continued on next page.)

OTHER PUBLICATIONS

Herman Feil et al. "Molecular separation by thermosensitive hydrogel membranes" *Journal of Membrane Science*, 64 (1991) 283–294.

(List continued on next page.)

*Primary Examiner*—Arlen Soderquist
*Assistant Examiner*—Brian R. Gordon

(57) ABSTRACT

Methods for selectively separating at least one component from a multi-component componant fluidic sample are provided. In the subject methods, the fluidic sample is introduced into a micro-fluidic device that includes at least one micro-valve made up of a phase reversible material. The multi-component fluidic sample is then contacted with the microvalve in a microfluidic device under conditions sufficient for the at least one component to enter the microvalve, while the remaining constituents of the fluidic sample remain outside of the microvalve. Also provided are kits for use in practicing the subject methods, where the kits include at least a microfluidic device having a microvalve and instructional material (or means for obtaining the same) on how to use the device in the subject methods. The subject devices find use in a variety of applications, including sample desalting and concentration applications.

13 Claims, 1 Drawing Sheet

U.S. PATENT DOCUMENTS

| | | | |
|---|---|---|---|
| 5,681,751 A | | 10/1997 | Begg et al. |
| 5,720,717 A | | 2/1998 | D'Andrea |
| 5,746,901 A | | 5/1998 | Balch et al. |
| 5,755,942 A | | 5/1998 | Zanzucchi et al. |
| 5,759,369 A | * | 6/1998 | Menchen et al. ............ 204/456 |
| 5,770,029 A | | 6/1998 | Nelson et al. |
| 5,869,004 A | | 2/1999 | Parce et al. |
| 6,001,232 A | * | 12/1999 | Chu et al. ................... 204/455 |
| 6,027,625 A | * | 2/2000 | Stein et al. ................. 204/466 |
| 6,130,098 A | * | 10/2000 | Handique et al. ........... 436/180 |
| 6,375,901 B1 | * | 4/2002 | Robotti et al. .............. 422/103 |
| 6,524,790 B1 | * | 2/2003 | Kopf-Sill et al. .............. 435/6 |
| 6,537,828 B1 | * | 3/2003 | Nakaya et al. .............. 436/514 |
| 2001/0023827 A1 | * | 9/2001 | Liu et al. .................... 204/605 |
| 2002/0027076 A1 | * | 3/2002 | Harding et al. ............. 204/469 |
| 2003/0116437 A1 | * | 6/2003 | Burns et al. ................ 204/453 |

OTHER PUBLICATIONS

Fan Xiang et al. "An Integrated Microfabricated Device for Dual Microdialysis and On–Line ESI–Ion Trap Mass Spectrometry for Analysis of Complex Biological Samples" *Ana. Chem.*, 1999, 71, 1485–1490.

Dean W. Matson et al. "Laser machined components for microanalytical and chemical separation devices" *SPIE* vol. 3519, 200–207.

Thomas A.J. Duke et al. "Pulsed–field electrophoresis in microlithographic arrays" *Electrophoresis* 1996, 17, 1075–1079.

* cited by examiner

METHODS AND USING CHEMICO-MECHANICAL MICROVALVE DEVICES FOR THE SELECTIVE SEPARATION OF COMPONENTS FROM MULTI-COMPONENT FLUID SAMPLES

TECHNICAL FIELD

The field of this invention is micro-fluidic devices.

BACKGROUND OF THE INVENTION

Carrying out chemical or biochemical analyses, syntheses or preparations, even at the simplest levels, requires one to perform a large number of separate manipulations on the material components of that analysis, synthesis or preparation, where such manipulations include, but are not limited to: measuring, aliquoting, transferring, diluting, concentrating, separating, detecting, etc. One step that is performed in many of the above described processes is the separation of one or more components from a multi-component fluid sample. Such separation steps are common in applications where a given sample is concentrated with respect to one or more of its constituents and/or "desalted."

In many situations, it is desirable to work with small volumes of fluid, e.g., from femtoliter to $\mu l$ quantities of fluid. Such situations include sample analysis in which small volumes of initial sample are analyzed; chemical synthesis, in which small quantities of chemical are desired and/or expensive reagents are employed; and the like. As such, there has been much interest in the development of micro-fluidic devices in which fluid is manipulated through one or more micro-channels present in the device.

Many of the above described manipulations easily lend themselves to such miniaturization and integration. For example, the use of these microfluidic technologies has been described in a number of applications, including, e.g., amplification (U.S. Pat. Nos. 5,587,128 and 5,498,392) and separation of nucleic acids (Woolley et al., Proc. Nat'l. Acad. Sci. 91:11348–352 (1994) and hybridization analyses (WO 97/02357 to Anderson).

However, not all of the above described manipulations have been successfully adapted to be carried out in a microfluidic device. One type of application that has not yet had great success in the microfluidic setting is the separation of components from a multi-component sample. While protocols have been developed or suggested to both concentrate and desalt a sample in a microfluidic device, these technologies are not entirely satisfactory for a number of reasons, e.g., unsuitability for use with a wide range of fluid samples, difficulty in fabrication of the microfluidic device, etc.

As such, there is great interest in the development of a technology that can easily and reliably perform sample separations in a microfluidic format. The present invention satisfies this need.

Relevant Literature

References of interest include: U.S. Pat. No. 5,869,004; as well as Matson et al., SPIE (1998) 3519:200; F. Xiang et al, Anal. Chem. (1999) 71:1485Feil et al., J. Membrane Sci. (1991) 64:283.

Micro-fluidic devices are described in U.S. Pat. Nos. 5,770,029; 5,755,942; 5,746,901; 5,681,751; 5,658,413; 5,653,939; 5,653,859; 5,645,702; 5,605,662; 5,571,410; 5,543,838; 5,480,614, the disclosures of which are herein incorporated by reference.

Reversible gel compositions are described in U.S. Pat. Nos.: 5,720,717; 5,672,656; 5,631,337; 5,569,364; 5,670,480; 5,658,981; 5,470,445; 5,432,245; 5,298,260; 5,162,582; 4,439,966, the disclosures of which are herein incorporated by reference.

SUMMARY OF THE INVENTION

Methods for selectively separating at least one component from a multi-component fluidic sample are provided. In the subject methods, the fluidic sample is introduced into a micro-fluidic device that includes at least one micro-valve made up of a phase reversible material. The multi-component fluidic sample is then contacted with the microvalve in the microfluidic device under conditions sufficient for the at least one component to enter, and often pass through, the microvalve, while the remaining constituents of the fluidic sample remain outside of the microvalve. Also provided are kits for use in practicing the subject methods, where the kits include at least a microfluidic device having a microvalve and instructional material, or at least means for obtaining the same, on how to use the device in the subject methods. The subject devices find use in a variety of applications, including sample desalting and concentration applications.

DESCRIPTION OF THE SPECIFIC EMBODIMENTS

Figure 1:
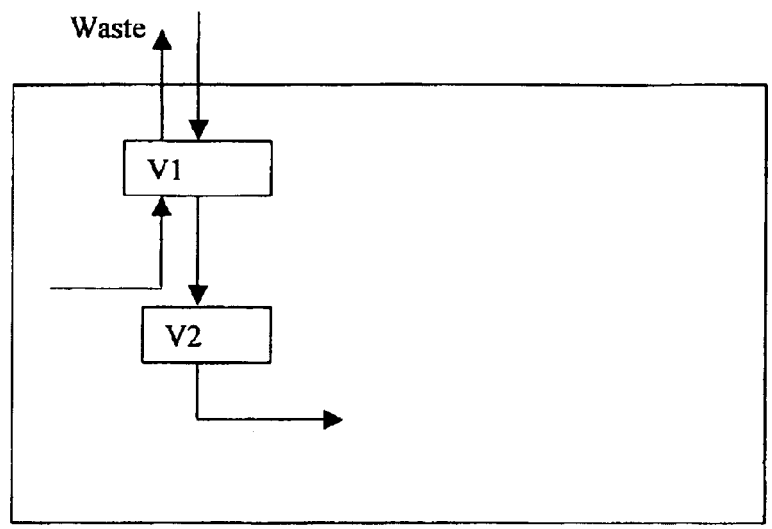
FIG. 1 provides a schematic view of a microfluidic device that can be used to desalt a sample according to the subject invention.

Methods for selectively separating at least one component from a multi-component fluidic sample are provided. In the subject methods, the fluidic sample is introduced into a micro-fluidic device that includes at least one micro-valve made up of a phase reversible material. The multi-component fluidic sample is then contacted with the microvalve in the microfluidic device under conditions sufficient for the at least one component to enter, and often pass through, the microvalve, while the remaining constituents of the fluidic sample remain outside of the microvalve. Also provided are kits for use in practicing the subject methods, where the kits include at least a microfluidic device having a microvalve and means for obtaining instructional material, or a means for obtaining the same, on how to use the device in the subject methods. The subject devices find use in a variety of applications, including sample desalting and concentration applications. In further describing the subject invention, the subject methods are discussed first in greater detail, followed by a review of various representative applications in which the subject methods find use and a description of the kits of the subject invention.

Before the subject invention is described further, it is to be understood that the invention is not limited to the particular embodiments of the invention described below, as variations of the particular embodiments may be made and still fall within the scope of the appended claims. It is also to be understood that the terminology employed is for the purpose of describing particular embodiments, and is not intended to be limiting. Instead, the scope of the present invention will be established by the appended claims.

In this specification and the appended claims, the singular forms a, an and the include plural reference unless the context clearly dictates otherwise. Unless defined otherwise, all technical and scientific terms used herein have the same meaning as commonly understood to one of ordinary skill in the art to which this invention belongs.

Methods

As reviewed above, the subject invention provides a method for separating at least one component from a multi-component fluidic sample. By multi-component fluidic sample is meant a fluidic sample that comprises a plurality of different components or constituents, i.e., a complex fluidic sample. By plurality of components is meant at least about 2, usually at least about 5 and more usually at least about 10, where the sample comprises even more distinct components in many embodiments, e.g., 50, 100, 200, etc. The multi-component fluidic sample is a sample with a low viscosity, where the viscosity of the sample generally does not exceed about 10 cP and usually does not exceed about 5 cP. In many embodiments, the sample is an aqueous sample, by which is meant that it includes water. Representative samples of interest that may be subjected to manipulation by the subject methods include, but are not limited to: physiological derived fluid samples, e.g., blood or a fraction/derivative thereof, saliva, urine, etc., biological samples, e.g., tissue and cell homogenates and derivatives thereof; and the like. The sample that is manipulated via the subject methods may be obtained and processed, where necessary, using any convenient protocol, where the particular protocol employed in any given sample procurement and processing step will necessarily depend on the nature of the sample to be manipulated.

Once the sample is obtained and any requisite/desired processing steps are finalized, the sample is introduced into a microfluidic device having at least one microvalve made up of a phase reversible material. A feature of the subject invention is that the microvalve of the microfluidic device plays a prominent role in the separation of the at least one component from the multi-component fluid sample. As the microfluidic devices, and particularly the microvalve(s) present therein, play such an important and central role in the subject methods, microfluidic devices that may be employed in the subject methods are now reviewed in greater detail.

As used herein, the term "micro-fluidic" device refers to any device in which micro-volumes of fluid are manipulated along a fluid flow path during any given use or operation, e.g., sample preparation, sample separation, chemical synthesis, etc., where "micro-volume" means from about 10 femtoliters to 500 $\mu$l, usually from about 100 femtoliters to about 200 $\mu$l. The micro-fluidic devices contain at least one fluid flow path through which fluid flows through the device, where a plurality of flow paths that may or may not be intersecting and may be positioned in any convenient configuration may be present in the device. Generally, the micro-fluidic device with which the subject methods are practiced have at least one micro-compartment positioned at some point in the fluid flow path, where the term "micro-compartment" means any type of structure in which micro-volumes of fluid may be contained, and includes micro-chambers, micro-channels, micro-conduits and the like. Depending on the nature of the micro-compartment, the micro-compartment may be the entire fluid flow path through the device, e.g., where the fluid flow path is a micro-channel, or occupy only a portion of the fluid flow path of the device. The term micro-chamber, as used herein, means any structure or compartment having a volume ranging from about 1 $\mu$l to 500 $\mu$l, having cross-sectional areas ranging from about 0.05 cm$^2$ with a chamber depth of 200 $\mu$m to 5 cm$^2$ with a chamber depth of 1 mm; usually from about 10 $\mu$l to 500 $\mu$l, having a cross-sectional area ranging from about 0.5 cm$^2$ with a chamber depth of 200 $\mu$m to about 5 cm$^2$ with a chamber depth of 1 mm; and more usually from about 20 $\mu$l to 200 $\mu$l, having a cross-sectional area ranging from about 1 cm$^2$ with a chamber depth of 200 $\mu$m to about 4 cm$^2$ with a chamber depth of 500 $\mu$m. The micro-compartment structure may have any convenient configuration, including square, circular, rectangular, octagonal, irregular etc. Micro-channels or micro-conduits are micro-compartments that are dimensioned or configured such that fluid is capable of flowing through the micro-channel by capillary flow, i.e., the micro-channel is of capillary dimensions. By capillary dimensions is meant a structure or container in which any cross-sectional dimension from one side to another, e.g., diameter, widest point between two walls of a channel, etc., does not exceed about 250 $\mu$m. Generally, any cross-sectional dimension of the micro-channel will range from about 10 to 250 $\mu$m, usually from about 50 to 200 $\mu$m. The flow through the micro-channels may also be pressurized.

The micro-channel(s) of the device may have a linear configuration, a curved configuration, or any other configuration, e.g., spiral, angular, etc., depending on the intended use of the device. In addition, there may be more than one micro-channel in the device, where the micro-channels may: (a) intersect at various points to form complicated flow paths or patterns through the device, e.g., Y-shaped intersections, T-shaped intersections, crosses; and (b) be separated by one or more micro-chambers, etc, depending on the intended use of the device.

In many embodiments, the micro-channel(s) of the microfluidic devices employed in the subject methods, as well as any other components, e.g., entry ports, etc., will be present in an essentially planar-shaped substrate, e.g., a card-shaped substrate, disk-shaped substrate, etc. The substrate may be fabricated from a variety of different materials, including polymeric substrates, such as polyimides, polycarbonates, polyesters, polyamides, polyethers, polyolefins, and mixtures thereof, as well as silicon or silicon dioxide based materials, such as quartz, fused silica, glass (borosilicates) etc, ceramics and composites thereof.

A variety of different micro-fluidic devices have been developed that may be modified to include at least one microvalve for use in the subject methods, where such devices include, but are not limited to, those described in: U.S. Pat. Nos. 5,770,029; 5,755,942; 5,746,901; 5,681,751; 5,662,787; 5,661,028; 5,658,413; 5,653,939; 5,653,859; 5,645,702; 5,632,876; 5,605,662; 5,599,432; 5,585,069; 5,571,410; 5,543,838; 5,540,826; 5,480,614; and 5,458,761; the disclosures of which are herein incorporated by reference. Of particular interest in many embodiments are the $\mu$-TAS devices described in U.S. Pat. Nos. 5,658,413; 5,571,410 and 5,500,071; the disclosures of which are herein incorporated by reference.

As indicated above, at least one micro-valve that modulates the flow of fluid along at least one fluid flow path in the device is present in the devices employed in the subject methods. The micro-valve of the subject devices is characterized by comprising a phase reversible material which modulates fluid flow along a flow path in the device. By phase reversible material is meant a material that changes its physical state, e.g., going from a permeable to an impermeable state or going from an impermeable to a permeable state, in response to an applied stimulus.

As such, the phase reversible material is a material that is capable of going from a first stage that is substantially permeable to fluid, i.e., allows free flow of fluid, to a second stage that is substantially impermeable to fluid i.e., substantially inhibits fluid flow. Specifically, the material is one that is capable of going from a first, porous state to a second, substantially non-porous state. Any phase reversible material may be employed, so long as the material changes in phase in response to an applied stimulus in a manner sufficient to modulate its fluid permeability, i.e., the ability of fluid to flow through the material. Put another way, the porosity of the phase reversible material varies in response to an applied stimulus, such that by applying various stimuli to the phase reversible material of the microvalve, the porosity of the microvalve and therefore its permeability to molecules of different molecular weight, may be varied or modulated, generally in a manner proportional to the applied stimulus and magnitude thereof.

The phase reversible material of the microvalve is a material that responds to an applied stimulus with at least a porosity or permeability change, if not a phase change depending on the magnitude of the applied stimulus. The material may be responsive to a number of distinct stimuli, where stimuli of interest include, but are not limited to: temperature, pH, electrical current, light, magnetic field, etc. Specific materials of interest as phase reversible materials are polymers.

In many embodiments, the phase reversible material is a reversible gel, where by reversible gel is meant a gel composition that is capable of changing its physical state, e.g., from soluble to semi-solid gel state, in response to a particular stimulus, e.g., temperature, pH, chemical agent, electrical current, light, etc. Such gel compositions are known in the art as "smart" gels, "intelligent" gels, hydrogels, etc. The subject micro-valves of this embodiment in which the phase reversible material is a gel composition may comprise any suitable phase reversible gel, as long as the gel is capable of changing its physical state, or at least porosity/permeability, in response to an applied stimulus.

Of particular interest in many embodiments of the subject invention are reversible gels that change their physical state, e.g., change their fluid permeability, by going from a first state of large pores to second state of small pores in response to a change in temperature, i.e., thermoreversible or temperature sensitive gels. The thermoreversible or temperature sensitive gels of the microvalves of the microfluidic devices that find use in the subject invention are those gels that are capable of changing their physical state, e.g., gels that go from a permeable to an impermeable state or an impermeable to a permeable state, over a narrow temperature range, e.g., the lower critical solution temperature (LCST). In the thermoreversible gels finding use as a phase reversible material in the micro-valves of the subject invention, both gels which go from a permeable to an impermeable form as well as gels that go from an impermeable to a permeable form as the temperature increases find use, where in many embodiments, those thermoreversible gels which go from a permeable to an impermeable form as the temperature increases of are particular interest.

A variety of thermoreversible or temperature sensitive gels have been identified and are suitable for use in the micro-valves of the microfluidic devices that find use in the subject invention. Thermoreversible polymeric gels of interest include those comprising polymers such as: partially saponified polyvinyl acetates, polyvinyl methyl ether, methyl cellulose, polyalkylene oxides, polyvinyl methyloxazolidinone, and polymacrylamides, and the like, where polyacrylamides and polyalkylene oxide based polymers are of particular interest.

Specific polyacrylamides of interest include: poly-N-ethylacrylamide; poly-N-n-propyl(meth)acrylamides; poly-N-isopropyl(meth)acrylamides; poly-N-cyclopropyl(meth)acrylamides; poly-N,N-diethylacrylamide; poly-N-methyl-N-ethylacrylamide; poly-N-methyl-N-n-propylacrylamide; poly-N-methyl-N-isopropylacrylamide; poly-N-acryloylpiperidine; poly-N-acryloylpyrrolidine; poly-N-tetrahydrofurfuryl(meth)acrylamide; poly-N-methoxypropyl(meth)acrylamide; poly-N-ethoxypropyl(meth)acrylamide; poly-N-isopropoxypropyl(metho)acrylamide; poly-N-ethoxyethyl(meth)acrylamide; poly-N-(2,2-dimethoxyethyl)-N-methylacrylamide; poly-N-1-methyl-2methoxyethyl(meth)acrylamide; poly-N-1-methoxymethylpropyl(meth)acrylamide; poly-N-(1,3-dioxolan-2-yl)-N-methylacrylamide; and poly-N-8-acrylyl-1,4-dioxa-8-azaspiro [4,5]decane, N-(2-methoxyethyl)-N-isopropylacrylamide; and the like. Of particular interest in this class of the thermoreversible polymeric compositions are those made up of N-isopropylacrylamide graft copolymers, where polymers of interest include graft copolymers of hydrophobic polymers, e.g. butyl methacrylate; and hydrophilic polymers, e.g. N,N-dimethylacrylamide. See also Takei et al., Bioconjugate Chem. (1993) 4:341–346, which discloses polymers of interest.

Also of particular interest are gels comprising polyalkylene oxides, particularly block copolymers of two or more different polyalkylene oxides, more particularly block copolymers of both hydrophobic and hydrophilic polyalkylene oxides. In many embodiments, block copolymers of polyethylene oxide and polypropylene oxide are preferred, particularly triblock copolymers thereof. Such copolymers are known in the art and sold under the tradenames PLURONIC™ and POLOXAMER™. Specific polyalkylene triblock copolymers of interest include: F-68, F-88; F-98; F-108, F-127 and the like, all available from BASF corporation.

In one type of microfluid device finding use in the subject invention, the micro-valve is made solely of the phase reversible material. In this embodiment, the phase reversible material may be positioned at one or more distinct locations along the fluid flow path, or along substantially the entire fluid flow path. Where the phase-reversible material occupies substantially the entire fluid flow path, during use its phase is generally switched from a fluid permeable to a fluid impermeable state at one or more distinct locations along the fluid flow path, but not along the entire fluid flow path.

Where the micro-valve consists essentially of the phase reversible material, the phase reversible material will be stably associated with the region of the device in which fluid flow modulation is desired. Stable association may be achieved in a number of ways, including bonding, and the like. In many embodiments, the phase reversible material may be bonded directly to the region of interest of the micro-fluidic device, where the nature of the bond may be covalent or non-covalent. For example, where the phase reversible material is a polymeric gel, the polymeric constituents of the phase reversible material may be bonded directly to the micro-compartment wall of the device in the region in which valve fluid control is desired, where the nature of the bond may be covalent or non-covalent, but will usually be covalent. The length of the micro-compartment occupied by the micro-valve in this second embodiment, i.e., the length of the micro-compartment to which the phase reversible material is stably associated, e.g., to which the polymeric components of the gel have been bound and in which the physical state of the gel is controllable, will vary depending upon the desired characteristics of the microvalve, i.e., strength, rate of fluid flow modulation, etc., but will generally be at least about 50 μm, usually at least about 100 μm and more usually at least about 500 μm long, and may be as long as 1 cm or longer, but will generally not exceed about 10 cm, and usually will not exceed about 5 cm. In the region of the micro-compartment occupied by the micro-valve, the phase reversible material will generally be stably associated, e.g., bonded, to all surfaces of the compartment in a manner that provides substantially no void space through which fluid may freely flow, e.g., the polymeric constituents of a phase reversible gel will be bonded to all of the surfaces of the micro-compartment, e.g., the top, bottom, left side and right side of a micro-channel having a cross-sectional square shape.

In other microvalve configurations, the phase reversible material is present in combination with one or more additional mechanical elements, such as a high surface area mechanical means, i.e., the micro-valve is a composite of a phase reversible material and a mechanical element, e.g., a reversible gel in combination with one or more high surface area components, e.g., rods, pins, etc, such as the structures described in U.S. Pat. No. 5,427,663, the disclosure of which is herein incorporated by reference. This embodiment is further characterized by having the high surface area stably associated with one or more walls of the flow path, as described in greater detail infra. The substantial surface area structures may be fabricated from a variety of materials, including quartz, fused silica, sapphire, polymeric materials, e.g., polyimides, etc. The substantial surface area structures of this embodiment (and therefore the phase reversible material associated therewith) are stably associated with the surface of the micro-compartment in which they are located. Stable association of the structures in the compartment is achieved in a number of ways, such as bonding of the structures to the micro-compartment surface. For example, the micro-valve may comprise a phase reversible material, (e.g., reversible gel) in combination with a plurality of polymeric rods covalently attached to one or more sides of the fluid flow path, e.g., micro-channel, where such a rod configuration is described in Austin et al., Electrophoresis (1996) 17:1075–1079. In such embodiments, the phase reversible material, e.g., the polymeric constituents of the reversible gel, will be attached to the high surface area component, e.g., rod or pin, either non-covalently or covalently, but usually covalently.

In yet another embodiment, the micro-valve comprises a phase reversible material in combination with one more high surface area components, where the phase reversible material/high surface area composite structure is not attached to one or more of the walls of the fluid flow path. Instead, the otherwise mobile or detached composite structure is retained at one or more locations along the fluid flow path with a retaining means, e.g., a mechanical restriction means. Examples of such means include: physical constrictions provided by appropriate configuration of the walls of the flow path, e.g., micro-compartment, in the region in which the phase reversible material is located; stably positioned frits, filters or other solid permeable structures positioned on either side of the phase reversible material in the fluid flow path of the device; and the like. The frits or analogous structural retention means keep the phase reversible material from shifting location in the flow path of the device. The mobile or detached high surface area component of the composite structure in this embodiment may vary widely. Suitable high surface area components of this embodiment include: beads or particles, e.g., porous silica beads, membranes, mesh structures, and the like.

The micro-valves present in the microfluidic devices employed in the subject methods are actuated by an actuation means, e.g., a switch, that is external to the device, where the actuation means actuates a phase reversing means that may be entirely external to the device or at least partially internal to the device. As such, the subject device may or may not further comprise one or more internal components of a means for reversing the phase of the phase reversible material in the micro-valve.

The phase changing means which influences the state of a micro-valve in any given device will necessarily depend on the nature of the phase reversible material in the micro-valve, and will be a means capable of applying the requisite stimulus to the material to achieve the desired phase change. Thus, the phase changing means may be a means capable of applying thermal energy, light, electrical current, chemical agents, hydrogen ions, etc., to the phase reversible material. For example, where the micro-valve comprises a thermosensitive gel, the phase changing means will be a means for changing the temperature of the gel in a manner sufficient to change to the phase of the gel from one state to another, e.g., soluble state to semi-solid or solid state. In other words, the phase changing means will be a means capable of taking the gel above and/or below the phase critical temperature or lower critical solution temperature of the gel. An example of such a temperature changing means is a resistance heater. Another example of a suitable temperature changing means is a Peltier device.

As mentioned above, the phase changing means may be completely external to the device, i.e., the phase changing means may be entirely peripheral to the device, or one or more components of, but generally not all of, the phase changing means may be internal to the device. For example, where the phase changing means is an external heating element on which the subject device is placed during operation, the entire phase changing means is external or peripheral to the device. Alternatively, where the phase changing means includes a resistor element integrated into the device which interacts with external circuitry to provide the requisite electrical current to the internal resistor, a portion or component of the phase changing means is internal to the device.

Microfluidic devices as described above, as well as methods for their fabrication, are further detailed in U.S. patent application Ser. No. 09/294,867, the disclosure of which is herein incorporated by reference.

As indicated above, the first step in the subject methods is to introduce the fluid sample, which or may not have been preprocessed, into the microfluidic device. The manner by which the fluid sample is introduced into the microfluidic device necessarily varies depending on the nature of the device, and may include injection, pipette, valve and the like. The volume of fluid that is introduced into the device may vary, but generally ranges from about 1 pl to 10 ml, usually from about 1 nl to 1000 μl and more usually from about 100 nl to 10 μl.

Following introduction of the sample fluid into the microfluidic device, the fluid is contacted with at least one microvalve made up of a phase reversible material (as described above) under conditions sufficient for at least one component of the multi-component fluid sample to separate from the remaining components of the multi-component fluid sample, e.g., by at least entering the valve, and often passing through it. Contact of the fluid sample with the valve may be achieved using any convenient protocol for moving fluid through the microfluidic devices. In certain embodiments, a differential pressure gradient is created inside the fluid flow channel(s) of the microfluidic device such that the fluid sample moves through the device. One convenient means of moving the fluid sample through the device is to introduce additional fluid, e.g., via injection into the device, etc., behind the fluid sample that moves or flushes the fluid sample along the flow path of the device, e.g., by creating an area of higher pressure behind the fluid sample and a concomitant pressure differential in the flow path of the device.

At some time prior to contact with the microvalve, the microvalve will have been modulated through application of the appropriate stimulus to have a pore size that selectively allows sample constituents that have a molecular weight below a threshold value to pass into, and often through, the microvalve while excluding sample constituents having a molecular weight above a threshold value. The manner in which the microvalve is modulated, e.g., the nature of and the magnitude of the applied stimulus, necessarily depends on the nature of the phase reversible material that makes up the microvalve.

For purposes of further illustration of the invention, the invention will now be further described in terms of microvalves that are made up of phase reversible polymeric materials that are substantially impermeable above a lower critical solution temperature (LCST) and which are permeable to varying degrees below the LCST. It should be understood, however, that the below described methods using such valves are readily adaptable to other types of microvalves, including microvalves that are substantially impermeable below their LCST but permeable above their LCST. Representative phase reversible polymeric materials from which microvalves may be prepared to produce microvalves that are substantially impermeable above an LCST but proportionally permeable as their temperature moves further below the LCST include, but are not limited to: N-isopropylacrylamide-copolymers and the like.

In those embodiments where the microvalve is made up of a polymer whose permeability proportionally increases as the temperature moves below the LCST but is substantially impermeable when at a temperature above the LCST, the temperature of the micro-valve and polymer from which it is made will have been modulated to provide for the desired porosity at some point prior to contact with the sample. For example, where the threshold molecular weight is about 1000 daltons, the temperature of the microvalve will have been changed prior to contact with the fluid sample to a temperature that provides for a pore size in the phase reversible polymeric material of the microvalve that selectively allows passage of molecules that have a molecular weight that does not exceed about 1000 daltons but excludes molecules of higher molecular weight. In many embodiments, this temperature will be a high temperature that is close to, but does not exceed, the LCST of the material. While this high temperature may vary depending on the nature of the phase reversible polymeric material of the microvalve, in many embodiments this high temperature ranges from about 20° to 100°, usually from about 25° to 80° and more usually from about 30° to 60° C.

In other embodiments where the threshold molecular weight is about 10,000 daltons, the temperature of the microvalve will have been changed prior to contact with the fluid sample to a temperature that provides for a pore size in the phase reversible polymeric material of the microvalve that selectively allows passage of molecules that have a molecular weight that does not exceed about 10,000 daltons but excludes molecules of higher molecular weight. In many embodiments, this temperature will be a medium temperature that is substantially below the LCST of the material but above room temperature. While this medium temperature may vary depending on the nature of the phase reversible polymeric material of the microvalve, in many embodiments this medium temperature ranges from about 25° to 70°, usually from about 30° to 60° and more usually from about 35° to 50°.

By selectively modulating the temperature of microvalve, as exemplified above, the porosity of the microvalve can be adjusted to allow selective passage of molecules through the microvalve that have a molecular weight below a threshold amount, and exclude molecules having a molecular weight above a threshold amount. As such, the temperature of the microvalve can be set to provide for a threshold molecular weight value that ranges from about 1000 to 100,000 daltons, where specific threshold values of interest in many instances include: 1000 daltons, 10,000 daltons, 100,000 daltons and the like.

Contact of the fluid sample with the temperature set microvalve as described above results in selective passage of at least one component of the fluid sample through microvalve, assuming a sufficient driving force, e.g., pressure differential, is present in the flow channel of the microfluidic device to provide for the movement of the at least one component at least into, and often through, the valve. Generally, a portion of the components of the sample will move into and through the valve, while the remainder of the sample components, i.e. constituents, will remain excluded from the valve. In this manner, the subject methods provide for selective separation of at least one component from a multi-component fluidic sample, i.e., separation of the at least one component from the remaining components of the multi-component fluidic sample.

Utility

The subject methods find use in a variety of different applications in which the separation of at least one component from a multi-component fluidic sample inside a microfluidic device is desired. One representative application in which the subject methods find use is in the desalting of a fluidic sample. In such applications, the fluid sample is contacted inside the microfluidic device with a microvalve whose porosity has been modulated to a have a threshold value of 1,000 daltons. Upon contact and in the presence of a sufficient driving force, e.g., pressure differential, sample constituents having a molecular weight that do not exceed about 1,000 daltons pass into, and through, the microvalve, where such constituents include salts and other low molecular weight analytes. In this manner, the sample is desalted. Another representative application in which the subject methods find use is the concentration of a fluid sample, where by concentration is meant the selective enrichment of one or more of the sample constituents in the sample, i.e., an increase in the amount of one or more of the sample constituents for a given volume of sample. For example, where one wishes to concentrate the sample with respect to all constituents having a molecular weight above 10,000 daltons, the sample is contacted with a microvalve whose temperature is set to provide a threshold value of 10,000 daltons. Contact results in passage of all of the sample constituents having a molecular weight below 10,000 and "stacking" of the remaining sample constituents at the polymer interface. The above describe desalting and concentration applications are merely representative of the different applications in which the subject methods find use.

Kits

Also provided are kits for use in practicing the subject methods. The kits typically at least include a microfluidic device that includes at least one microvalve made up of a phase reversible material, as described above. The kits may further include a phase reversing means or components thereof, e.g., a heating means. The kits of the subject invention will also typically include: (a) instructions for practicing the subject methods with the microfluidic device; and/or (b) means for obtaining such instructions from a remote location, e.g., an internet website address, where the website contains the instructions for practicing the methods. The instructions or means for obtaining the same from a remote source will be recorded onto a substrate, where the particular substrate necessarily depends on the form of the instructions/means for obtaining the same. For example, where the instructions/or means for obtaining the same are in a print format, they will typically be recorded onto a printable substrate, e.g. paper, where the substrate may be the packaging, labeling or a package insert of the kit, etc. Where the instructions/means for obtaining the same are present in electronic format, they will be present on an electronically recordable, e.g., computer readable, medium, e.g., floppy disk, CD, digital tape, etc. In addition, the kits may comprise one or more additional elements that find use in the particular application for which the device has been fabricated, such as: elements used in electrophoretic or chromatographic applications, such as a separation medium, labels for use in separation, buffer mediums, and other reagents for practicing electrochromatographic and liquid chromatographic protocols; etc.

The following examples are offered by way of illustration and not by way of limitation.

Experimental
I. Synthesis of Microvalve Testing Device
A. Synthesis of Micro-Valve on Nylon Substrate Nylon mesh filters (Spectrum #148130) with 5 μm opening were treated with a solution of 3.72 g of calcium chloride and 3.72 g of water in 20 ml methanol for 20 min at 50° C. The filter was then placed into 20 ml of 3.6 M HCl for 40 min at 45° C. Finally, the substrate was left in water for 20 hr.

This nylon substrate was covered with a solution of 50 mg of sulfo-HSAB dissolved in 5 ml of phosphate buffer (pH 8.5). The substrate was left in the dark at room temperature overnight, then rinsed with water and air-dried.

Approximately 1 g of the temperature-sensitive polymer was dissolved in 10 ml of water. This solution was placed over the azido-activated nylon substrate and exposed to UV light at 265 nm for ca. 30 min from a distance of 3–6 cm. The nylon substrate was then rinsed with water and air-dried.

B. Valve Set Up

A polymer-modified nylon substrates was prepared as described above. The polymer-modified nylon substrate or valve was placed into a high pressure semi-prep filter assembly (Upchurch Scientific #A330) fitted with 2 short capillary lines (in and out). The assembly was fitted into a drilled hole within an aluminum block. The block was controlled by a Peltier device and heat sink. The device allowed warming and cooling of the block and the filter assembly to within 1° C. accuracy. Fluids flowed through the nylon substrate (valve) and filter assembly via applied pressure on the fluid introduction syringe via the entry line.

II. Testing
A. Stock Solution

A stock solution was made as follows:

A 100 ml stock solution containing 5.8 g NaCl; 2 mg Danzyl Phenylalanine; 2 mg Danzylserine; 1 mg Angiotensin (1046 MW) and 1 mg Bradykinin (1060 MW) and water was prepared.

B. Injection

The entrance line to the device described in I.B above was attached to a 5 ml syringe. The device and valve assembly therein was set to 48° C. to render the valve impermeable by substantially closing the pores. The device was maintained at this temperature for 5 minutes. The syringe was then loaded with 5 ml of stock solution and aliquots were run through the valve as follows:

| Valve Temperature in ° C. | Collect ~0.5 ml (vial #) |
|---|---|
| 45 | 1 |
| 44 | 2 |
| 43 | 3 |
| 41 | 4 |
| 39 | 5 |
| 37 | 6 |
| 35 | 7 |
| 32 | 8 |

Each of the resultant vials was then analyzed by HPLC.

C. HPLC Analysis
1. Calibration

The LC column was a VYDAC column C-18 peptide/protein column. A sequence of 5 runs was performed on the stock solution described above as follows: injection=5 ml; A gradient solvent system was used that begins with 100% $H_2O$ (0.1% TFA) & runs to 50% $H_2O:CH_3CN$ at the end of the 30 min; this is followed with 5 min 90% $CH_3CN$ (0.1% TFA). Column temperature=37°.

Following the above protocol, four peaks were observed: 15 min/21 min/22 min and 23.5 min.

The middle two peaks were confirmed to be angiotensin and bradykinin.

2. HPLC Analysis of Vials Prepared in II.B

All 9 vials prepared in II.B above were analyzed by HPLC. The peptide hormones appears in vials 2 to 7.

Vials 1 to 3 were analyzed by HPLC as described above. Vial 1 shows both amino acids and potentially some peptide. In Vial 2, the peptides Angiotensin II and Bradykinin begin to appear, with the hydrophilic peptide being the more prominent of the two. In Vial 3, all four stock solution components are present.

The above results demonstrate that the porosity of the valve proportionally changes as the temperature decreases and that microfluidic separation according to the methods of the subject invention works.

III. Representative Applications
A. Desalting

Sample is introduced into the microfluidic device shown in FIG. 1. The microfluidic device of FIG. 1 has two temperature sensitive valves, V1 and V2. The temperature of V1 is first set just below the LCST such that only molecules having a molecular weight of less than about 1000 daltons are capable of passing through the valve. As sample passes through the device in the direction of the indicated arrows, low molecular weight solutes, e.g., salts, pass through valve V1 and are sent to waste, while the remaining constituents stack up on the upstream side of the valve. The temperature of the valve is then brought down to room temperature and fluid is flushed in the opposite direction through V1 towards V2, carrying the sample constituents towards V2. V2 is set at a temperature that provides for a porosity in V2 that excludes passage of any constituents having a molecular weight in excess of 10,000 daltons. As such, the fluid that passes through V2 and onward for further processing/manipulation in the microfluidic device is one that contains species that range in size from 1000 to 10,000 daltons.

B. Concentrating

Figure 2:
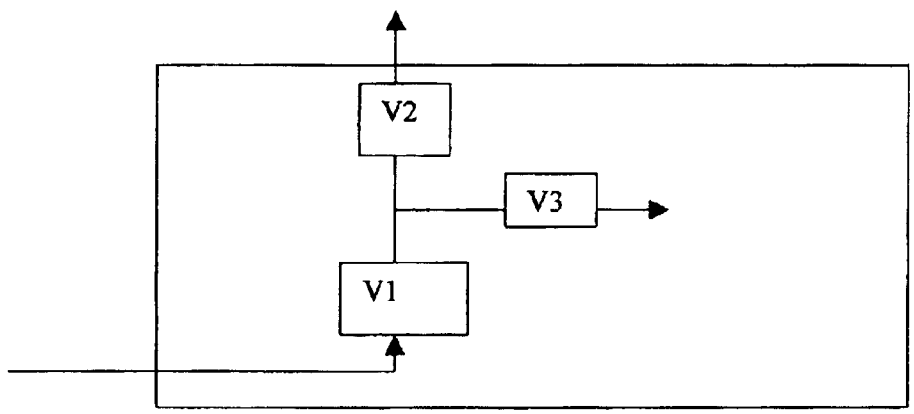
FIG. 2 provides a schematic view of a microfluidic device that can be used to concentrate a sample according to the subject invention.

The device shown in FIG. 2 having three temperature sensitive valves: V1, V2 and V3; is used according to the following parameters. In a first state, the temperature of V1 is close to the LCST, the temperature of V2 is room temperature and the temperature of V3 is greater than the LCST. In the second state, the temperature of V1 is at a state where molecules in excess of 10,000 daltons do not pass through it; the temperature of V2 is greater than LCST and the temperature of V3 is room temperature. Fluid is passed through the microfluid device under the first state and then under the second state. As a consequence, effluent from V3 is desalted and concentrated, and contains sample components having a molecular weight of from 1000 to 10,000 daltons.

It is evident from the above results and discussion that the subject invention provides for simple and effective methods for selectively separating sample constituents of a multi-component fluidic sample in a microfluidic device format. The subject methods overcome disadvantages associated with placement of traditional chromatographic media into a microfluidic device, e.g., excessive pressure buildup, or placement of dialysis membranes into a microfluidic device, e.g., incomplete sealing of membrane and flow channel, and provide for proportional control of the porosity of the microvalve separation means, which is not achievable with other technologies. As such, the subject invention represents a significant contribution to the art.

All publications and patent applications cited in this specification are herein incorporated by reference as if each individual publication or patent application were specifically and individually indicated to be incorporated by reference. The citation of any publication is for its disclosure prior to the filing date and should not be construed as an admission that the present invention is not entitled to antedate such publication by virtue of prior invention.

Although the foregoing invention has been described in some detail by way of illustration and example for purposes of clarity of understanding, it is readily apparent to those of ordinary skill in the art in light of the teachings of this invention that certain changes and modifications may be made thereto without departing from the scope of the appended claims.

What is claimed is:

1. A method for selectively separating components having a molecular weight below a threshold value from a multi-component fluidic sample, said method comprising:

introducing said multi-component fluidic sample into a micro-fluidic device having a fluid flow path and at least one micro-valve comprising a phase reversible gel material having a first porosity that can be modulated in response to an applied stimulus to provide a second porosity; and contacting said introduced multi-component fluidic sample with said micro-valve under conditions sufficient for said components of said multi-component fluidic sample having a molecular weight below said threshold value to at least move into said micro-valve while the remaining components of said multi-component fluidic sample having molecular weights above said threshold level are excluded from entering said micro-valve and thereby remain outside of said micro-valve;

wherein said method comprises modulating the porosity of said micro-valve by applying said stimulus to said gel having said first porosity to provide said gel with said second porosity that selectively allows sample components that have a molecular weight below said threshold value to at least move into said micro-valve while excluding entry into said micro-valve of sample components having molecular weights above said threshold value.

2. The method according to claim 1, wherein said phase reversible material is a phase reversible polymer.

3. The method according to claim 1, wherein said phase reversible material is thermo-reversible.

4. The method according to claim 1, wherein said stimulus is a change in temperature.

5. The method according to claim 1, wherein said threshold value is about 1000 daltons and said method is a method of desalting said multi-component fluidic sample.

6. A kit for use in selectively separating at least one component from a multi-component fluidic sample, said kit comprising:

(a) a micro-fluidic device having a fluid flow path and at least one micro-valve comprising a phase reversible material; and (b) at least one of:
(i) instructions for practicing the method of claim 1; and
(ii) means for obtaining instructions for practicing the method of claim 6; wherein said instructions and means for obtaining the same are recorded onto a substrate.

7. The kit according to claim 6, wherein said substrate is a printable substrate.

8. The kit according to claim 6, wherein said substrate is an electronically recordable substrate.

9. The kit according to claim 6, wherein said kit further comprises a phase reversing means.

10. A method for concentrating a multi-component fluidic sample with respect to at least one constituent thereof, said method comprising:

introducing said multi-component fluidic sample into a micro-fluidic device having a fluid flow path and at least one micro-valve comprising a phase reversible gel material having a first porosity that can be modulated in response to an applied stimulus; and contacting said introduced multi-component fluidic sample with said micro-valve under conditions sufficient for components of said multi-component fluidic sample having a molecular weight below a threshold value to at least move into said micro-valve while the remaining components of said complex fluidic sample having a molecular weights mabove a threshold level are excluded from entering said micro-valve and thereby remain outside of said microvalve;

wherein said method comprises modulating the porosity of said micro-valve by applying said stimulus to said gel having said first porosity to provide said gel with said second porosity that selectively allows sample components that have a molecular weight below said threshold valve to at least move into said micro-valve while excluding entry intosaid micro-valve of sample components having molecular weights above said threshold valve, and further: wherein said multi-component fluidic sample is concentrated with respect to at least one constituent thereof.

11. The method according to claim 10, wherein said phase reversible material is a phase reversible polymer.

12. The method according to claim 10, wherein said phase reversible material is thermo-reversible.

13. The method according to claim 10, wherein said stimulus is a change in temperature.

* * * * *